(12) United States Patent
Stafström (10) Patent No.: US 6,221,250 B1
(45) Date of Patent: Apr. 24, 2001

(54) METHOD OF PREPARING A LIQUID MIXTURE

(75) Inventor: Nils Stafström, Uppsala (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/125,919
(22) PCT Filed: Feb. 24, 1997
(86) PCT No.: PCT/SE97/00301
 § 371 Date: Sep. 23, 1999
 § 102(e) Date: Sep. 23, 1999
(87) PCT Pub. No.: WO97/31692
 PCT Pub. Date: Sep. 4, 1997

(30) Foreign Application Priority Data

Feb. 29, 1996 (SE) .................................................. 96 00796

(51) Int. Cl.⁷ ..................................................... B01D 15/08
(52) U.S. Cl. ........................ 210/656; 210/101; 210/198.2
(58) Field of Search ..................................... 210/635, 656, 210/659, 198.2, 101; 530/413, 417

(56) References Cited

U.S. PATENT DOCUMENTS

| 3,615,170 | * | 10/1971 | Hazen ........................................ 23/22 |
| 3,712,513 | * | 1/1973 | Ashmead ............................ 210/198.2 |
| 4,699,717 | * | 10/1987 | Riesner ................................. 210/635 |
| 4,902,783 | * | 2/1990 | Goda ..................................... 530/415 |
| 5,209,853 | * | 5/1993 | Lynch .................................... 210/656 |
| 5,340,731 | * | 8/1994 | Kilburn ................................. 435/179 |
| 5,531,791 | * | 7/1996 | Wolfinbarger .......................... 623/16 |
| 5,610,285 | * | 3/1997 | Lebing ................................... 530/416 |
| 5,714,320 | * | 2/1998 | Kool ......................................... 435/6 |

FOREIGN PATENT DOCUMENTS 691 148 * 10/1996 (EP) ................................. 210/198.2

* cited by examiner

Primary Examiner—Ernest G. Therkorn
(74) Attorney, Agent, or Firm—Royal N. Ronning, Jr.

(57) ABSTRACT

A method of preparing a liquid mixture of controlled pH including (i) one or more buffering species, (ii) an acid or alternatively a base, (iii) optionally a salt; and (iv) a solvent wherein the proportions of the different components ((I) to (iv)) of the mixture are concomitantly varied in such a way as to take into account of the interrelationship of the ionic strength and the pH of the mixture.

12 Claims, 9 Drawing Sheets

METHOD OF PREPARING A LIQUID MIXTURE

REFERENCE TO RELATED APPLICATIONS

This application is a 371 of PCT/SE/00301 filed Feb. 24, 1997.

1. Technical Field

The present invention relates to a method of generating a liquid mixture of controlled pH, as well as to an apparatus applicable in such a method.

More specifically the invention relates to a method of liquid chromatography using a liquid mixture such as mentioned above, as well as to an apparatus, applicable in such a chromatographic method.

The invention is of special interest in performing ion exchange chromatographic gradient elutions, more specifically for the separation and purification of biomolecules such as proteins.

2. Background and Prior Art

Obtaining liquid media of precisely known composition is in many cases important, as e.g. in the field of liquid chromatography. However, in many chromatographic separations the composition of the liquid media should not only be at each moment precisely known and controlled, but also should vary with time in a precise and controlled manner, as during a gradient elution.

Different liquid chromatographic modes exist, based on the different interactions of the molecules to be separated with the stationary phase on which they are retained and the mobile phase, i.e. the eluent. Especially in the ion exchange chromatographic mode, where the stationary phase is constituted of ion exchange resins, the gradient elution method is widely used; the eluent contains an inert salt and the gradient is performed by varying the concentration of this salt. This is a very important method for the separation and purification of biomolecules such as proteins. See e.g. Warren W., et al. "A new strategy for rapid optimization of protein separations", American Biotechnology Laboratory, 0749-3223, 34-40, (1989).

The possibility of separating the proteins on ion exchange resins is due to the fact that the protein molecule in general is charged at different sites. It is the presence of these charges that makes the proteins susceptible to separation by the retention on ion exchange columns.

These charges of the protein molecule originate from the acidic/basic character of its amino acid residues, prone to protonations or deprotonations. It is obvious that the charges at the different sites of the molecules, and hence the net charge of the same, will be significantly influenced by the pH of the surrounding liquid media, thereby making protein separation by ionic chromatography highly susceptible to the pH of the liquid medium, i.e. the eluent. See e.g. Diamond P. F., Carberry R., "Systematic Methods of Development for Chromatography of Biomolecules: pH Mapping", BioConcepts, Technical Newsletter of PerSeptive Biosystems, Sep.–Oct., 1–3, (1990).

In accordance with the above, it has been well documented that the pH and ionic strength of the eluent are the two most important parameters that control selectivity of protein separations on ion exchange resins.

The traditional way of gradient formation has involved the careful preparation of eluents comprising inert salts as well as buffers of predetermined pH to effect the ionic strength gradient at constant pH.

The optimization of the separation of the proteins has been accomplished by changing the slope of the inert salt gradient and/or replacing the buffer system by one with a different pH.

In the prior art, the optimization thus has included the preparation of numerous buffer solutions with predetermined pH and salt concentrations, which have to be meticulously titrated for the separations to be reproducible.

The above described methods, which herein below will be referred to as the "traditional" methods, being very time consuming and awkward, Warren et al. (ibid.) proposed a new procedure, which they called the Waters Auto-Blend™ method, wherein pH, ionic strength and gradient profiles are automatically generated using a single set of stock solutions. These stock solutions are: an acidic buffer, a basic buffer, a salt solution and deionized water (Milli-Q water). By a precise blending of these four solutions, Warren et al. create different gradients, of the ionic strength as well as the pH. In fact, Warren et al. separately blend the two buffer solutions, i.e. the acidic and the basic one, to obtain a certain preselected pH, and then combine this blend with a similar blend of the salt solution and the deionized water with an equally predetermined ionic strength. By varying either the proportion of the salt solution to the water, or of the acidic buffer to the basic one, they create, what they call, independent gradients of either the pH or the ionic strength, or alternatively change the pH from one run to another without having to chose an entirely new buffer system.

(An automatized variety of this method is called the BioCAD™ method, which nevertheless works according to the very same principle, and also belongs to the same society, the PerSeptive Biosystems Inc., Massachusetts, US.) Warren et al. thus reduce the great number of complex buffer solutions which had to be prepared in the traditional methods in optimizing a given protein separation with respect to the pH, to only two different buffer solutions and a salt solution, the latter one being of a much simpler preparation.

A major drawback with the method of Warren et al. is that it in fact fails to provide an eluent of a precisely controlled pH as well as ionic strength. This is due to the fact that they do not take account of the interrelationship of the ionic strength and the pH. However, by considering the Debye-Hückel equation, wellknown from many textbooks in physical or inorganic chemistry, such as "Physical Chemistry" by P. W. Atkins (Oxford university press ISBN 019 855148 7) and "Buffers for pH and Metal Ion Control" by D. D. Perrin, Boyd Dempsey (Chapman and Hall laboratory manuals ISBN 0 412 11700 2), incorporated herein by reference, one realizes that as the ionic strength varies during a salt gradient, the pH will also vary. In view of the foregoing discussion of the importance of the pH to the binding behaviour of the proteins, the failure to control, in a very precise manner, the pH of the eluent appears to be a significant drawback for an efficient optimization of a protein separation: a small variation of pH can entrain an important variation in the retention behaviour of a protein molecule in an unpredictable way.

It appears that the optimization of a protein separation is greatly impaired by the failure to provide an eluent of very precisely known pH in an easy and convenient way. The traditional methods, on the one hand, have been very cumbersome, sometimes making the careful optimization of a protein separation impossible because of a lack of time and/or money. The method of Waters et al., on the other hand, which is said to simplify the optimization, in fact is inherently inaccurate as to the real pH of the eluent in the system during any salt gradient.

SUMMARY OF THE INVENTION

The object of the present invention is to provide a method of preparing a liquid mixture of varying ionic strength wherein the pH can be controlled in a precise and reproducible way.

This object is achieved by a method of preparing a mixture comprising the following components:

(i) one or more buffering species;
(ii) an acid or alternatively a base;
(iii) optionally a salt; and
(iv) a solvent wherein the proportions of the components (i) to (iv) are concomitantly varied in such a way as to take account of the interrelationship of the pH and the ionic strength of the liquid mixture to obtain at each moment a preselected pH of the mixture.

The inventive method is based on the use of a modified Debye-Hückel equation. It comprises the steps of, (a) calculating, by the use of the Debye-Hückel equation, the proportions of the different protolytic components of a mixture as defined herein above having a given salt concentration, wherein the ionic strength of said mixture is taken to be due only to the presence of said salt, to obtain a preselected pH of said mixture;

(b) on the basis of the proportions calculated in the preceding step, calculating the resulting ionic strength of the mixture;

(c) by use of the Debye-Hückel equation and taking account of the ionic strength calculated in (b), calculating a new set of proportions of the protolytic components of the mixture at the preselected pH of the mixture; and (d) repeating the steps (b) and (c) until the deviation between the last set of values found for the proportions of the protolytic components and the set found in the immediately preceding step does not exceed a predefined maximum level, this last set of proportions then being retained as yielding the mixture of the selected pH at the given salt concentration.

Another object of the invention is to provide a method of generating a liquid flow of controlled pH wherein the liquid flow is obtained by feeding said components (i) to (iv) by means of a metering device which is governed by the above defined iterative procedure. This liquid flow is especially well suited as an eluent in ion exchange chromatography.

The invention also provides an apparatus for liquid chromatography wherein the above mentioned metering device is used to obtain the liquid eluent mixture of the invention.

BRIEF DESCRIPTION OF THE FIGURES

The invention will now be described in detail with reference to the figures, in which.

DESCRIPTION OF THE PREFFERED
EMBODIMENTS OF THE INVENTION

The components (i) to (iv)

In the present method, the component (i) can be a mixture of several different buffer species, e.g. up to five species, each with up to three different $pK_a$'s, enabling a wide pH range to be covered.

In the tables 1 and 2 herein below, some examples of preferred buffers are given, in association with the data for the respective buffers. The buffers called AIEX (Anion Exchange Chromatography) and CIEX (Cation Exchange Chromatography) respectively comprise:

AIEX: 0.05M 1-methyl piperazine, 0.05M Bis-Tris, 0.025M Tris;

CIEX: 0.03M $Na_2HPO_4$, 0.03M Na Formate, 0.06M Na Acetate.

TABLE 1

AIEX buffer data
Gradient 0.0–1.0M NaCl

| Buffer | pKa | Titrate with | ~pH range | Correction factors 0% B | 100% B | Notes |
|---|---|---|---|---|---|---|
| AIEX mixture | | 0.1M HCl | 5.0–9.5 | 0 | 0 | |
| 0.1M N-methyl-piperazine | 9.0 4.54 | 0.1M HCl | 8.4–10.3 5.0–5.7 | 0.0 −0.1 | −0.1 −0.2 | 3, 4 |
| 0.1M Bis-Tris | 6.37 | 0.1M HCl | 5.8–7.7 | +0.2 | 0.0 | |
| 0.1M Piperazine | 9.81 6.55 | 0.1M HCl | 9.2–10.5 6–6.7 | −0.1 −0.2 | −0.3 −0.4 | 4 |
| 0.1M Tris | 8.06 | 0.1M HCl | 7.5–8.5 | 0.0 | −0.2 | |

TABLE 2

CIEX buffer data
Gradient 0.0–1.0M NaCl

| Buffer | pKa | Titrate with | ~pH range | Correction factors 0% B | 100% B | Notes |
|---|---|---|---|---|---|---|
| CIEX mixture | | 0.1M HCl | 3.0–7.5 | 0 | 0.2 | |
| 0.1M Acetate Na | 4.76 | 0.1M HCl | 3.8–5.7 | 0.0 | −0.1 | |
| 0.1M Bicine | 1.84 | 0.1M | 7.0–9.0 | +0.1 | 0.0 | 1,2 |

TABLE 2-continued

CIEX buffer data
Gradient 0.0–1.0M NaCl

| Buffer | pKa | Titrate with | ~pH range | Correction factors 0% B | 100% B | Notes |
|---|---|---|---|---|---|---|
|  | 8.33 | NaOH |  |  |  |  |
| 0.03M Citrate Na₃ | 3.13 4.76 6.40 | 0.1M HCl | 2.5–6.2 | 0.0 | −0.2 | 4 |
| 0.1M Formate Na | 3.75 | 0.1M HCl | 2.5–4.5 | 0.0 | −0.2 |  |
| 0.03M Phosphate Na₂HPO₄ | 2.15 7.20 12.33 | 0.1M HCl | 6.2–7.6 2.2–3.3 | 0.0 0.0 | −0.3 −0.3 |  |
| 0.1M HEPES | ~3 7.39 | 0.1M NaOH | 6.6–8.2 | +0.2 | +0.3 | 1,2 |
| 0.1M MES | 6.18 | 0.1M NaOH | 5.5–6.7 | +0.1 | +0.1 | 2 |

Notes:
1. Zwitterionic
2. pKa and pKa/dT see ref. "Dissociation constants of organic bases in aqueous solution 2, supplement 1972" publ. Butterworths scientific publications ISBN 0 408 70408 X.
3. pKa and pKa/dT empirically determined.
4. pH range can not be extended beyond nominal pKa due to pKa drift with salt gradient.

As can be seen from the table, a pH range of 5.0 to 9.5 is covered by the buffer called AIEX, whereas a pH range of 3.0 to 7.5 is covered by the buffer called CIEX. Other buffer compositions may be used as well, depending on what pH range one wants to cover.

In the above tables, correction factors "0%B" and "100%B" are given. These correction factors will be explained herein below in the description of the iterative procedure.

In the description of the iterative procedure it further will be referred to protolytic systems, i.e. acid-base systems governed by the equilibrium constants of the protolysis reactions. A buffer species thus constitutes a protolytic system, whereas it will be noted that e.g. the AIEX and the CIEX buffers as defined herein above each one contain three protolytic systems i.e. three buffer species.

The acid of component (ii) can theoretically be any acid, but preferably is a strong acid, such as hydrochloric acid (HCl), which in solution is entirely dissociated. Similarly it is preferred that the base be a strong base, such as NaOH, although other bases also are equally possible. As indicated in the table, a suitable concentration of the acid or the base stock solution respectively is 0.1M, although other concentrations are equally possible.

The salt of component (iii) preferably is any salt which is inert to the liquid system, i.e. does not react in the system by any other way than by ionic dissociation. Preferable examples are NaCl or KCl. However, the invention could easily be extended to the use of pH active salts, e.g. ammonium sulphate, and it is considered to be within the knowledge of the person skilled in the art to make the corresponding modifications to the system.

It is considered to be within the knowledge of the person skilled in the art to select the proper salt gradient, depending on the other chromatographic conditions, such as the column etc. A preferable example however is an inert salt gradient of 0 to 1.0M.

The solvent of component (iv) could be any solvent or combination of solvents in which the other components of the liquid mixture are soluble, but preferably is distilled and/or deionized water. In case another solvent than water is used, it however preferably is in admixture with water, whereby the pH of the aqueous solvent may be taken to be that of the water phase.

The Iterative Procedure

The Debye-Hückel equation which provides the basis for the method of the invention is:

$$-\log f_i = A z_i^2 \frac{\sqrt{I}}{1+\sqrt{I}}$$

wherein $f_i$ is the activity factor of the ion i bearing a positive or negative charge of the absolute value $z_i$; I is the ionic strength of the ionic solution containing n different species of ions, I being obtained by the summation equation $$I = \frac{1}{2}\sum_{i=1}^{n}(C_i Z_i^2)$$

wherein $c_i$ for each type of ion i is equal to the concentration thereof.

The constant A in the equation varies with the temperature approximately according to the relationship $dA/dT=0.01°$ C. At a temperature 25° C., approximately A=0.512. It is considered to be within the knowledge of the person skilled in the art to make the corrections for the temperature dependence of A, if necessary.

In the method of the invention, to determine the proportions of the different components ((i) to (iv), supra) of the mixture an iterative procedure is adopted as outlined herein above. This iterative procedure will now be further described.

In a first step of this iterative procedure, the ionic strength of the liquid mixture of the components (i) to (iv) is set to be due only to the presence of the salt in the mixture, and by this hypothetic ionic strength the proportions of the different protolytic constituents of the system is calculated as a function of the selected pH by use of the Debye-Hückel equation. From this first step, the concentrations of the different species of the buffer system are derived.

In the second step, a more accurate value of the ionic strength of the liquid mixture of the components (i) to (iv) is calculated, taking account also of the contribution to the ionic strength from the ionic species of the buffer system, by use of the concentrations calculated in the previous step.

In the third step, the selected pH of the liquid mixture in combination with the ionic strength obtained in the second step is used in conjunction with the Debye-Hückel equation to calculate a new set of concentrations for the buffer species in the liquid mixture.

The steps two and three are then repeated a number of times, until the difference between the values obtained for the concentrations of the buffer species from one step to the one immediately following does not exceed a certain, preselected limit; these concentrations then correspond to the required proportion of the buffer component in the final mixture of controlled pH and ionic strength. The preselected limit may be e.g. a function of the start concentration of the buffer, e.g. 0.1% of the initial concentration of the buffer. However, the limit value preferably should be such as to reach the accuracy of the metering system, i.e. the pump and valve system.

For each value of the salt concentration and of the pH in the mixture, this iterative procedure will be repeated.

In a preferred embodiment, a correction factor is included in the calculations (factors termed 0%B and 100%B in tables 1 and 2 herein above). This correction factor is determined on an empirical basis, by measuring the deviation of the actually measured pH of the liquid mixture from the one that had been selected, at the minimum salt concentration, e.g. 0% salt, and at the maximum salt concentration, e.g. where the combined components (iii) and (iv) of the mixture are constituted only of the salt solution, i.e. 100% of (iii). If a certain deviation is found at 0% salt, the setpoint pH will be corrected by subtracting this deviation from the initial value of the setpoint pH; this correction will yield a new value for the proportion of the buffer species in the mixture at 0% salt. The corresponding correction is made at 100% salt, and the correction of the buffer proportion at each value of the salt concentration between the maximum and the minimum is obtained by a simple relation between these two extremes.

In a preferred embodiment, applicable e.g. in a liquid chromatographic system, the calculations are done by a data program, implemented from the equations given herein below, governing directly a metering device, such as a pump and valve system, or any other equivalent means of feeding the components. This program also includes correction factors for the variation of the $pK_a$'s with the temperature.

It will be noted that it is considered to be within the capacity of the man skilled in the field of the art to perform the above mentioned implementation on the basis of the equations given herein below.

In the implemented data program, the parameter which is calculated is the proportion of the buffer solution. A detailed description of the calculations performed will now be given. The understanding of the system might be facilitated by the FIG. 1, wherein the flow system is schematically represented and to which the description will now be referring.

Figure 1:
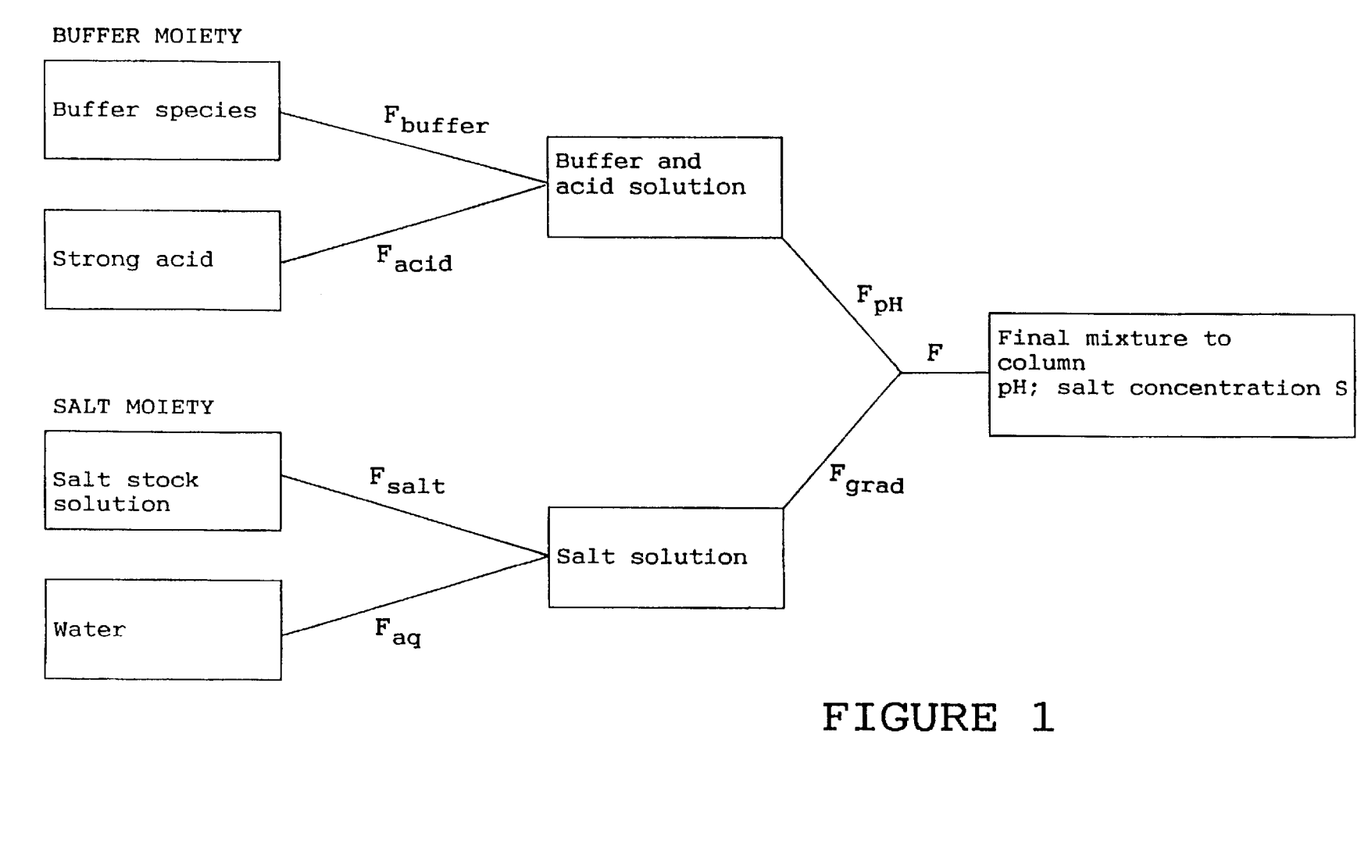
FIG. 1 is a schematic view of a flow system according to the invention.

The denotations in the figure are:

$F_{buff}$=the feeding flow of the buffer solution;

$F_{acid}$=the feeding flow of the acid solution (in the represented case where an acidic pH is sought; in case a basic pH is preferred the acid is replaced by a base);

$F_{salt}$=the feeding flow of the salt solution;

$F_{aq}$=the feeding flow of the water.

The buffer and acid solutions are fed together by way of a valve and pump system, metering very exactly the two components in the proportions calculated by the data program, consequently:

$F_{pH} = F_{buff} + F_{acid}$.

Another pump and valve system meters the salt solution and the water according to a selected salt gradient in a combined flow:

$F_{grad} = F_{salt} + F_{aq}$.

And the final eluent flow is:

$F = F_{pH} + F_{grad}$, this flow is taken to be constant.

Moreover, $F_{pH}$ and $F_{grad}$ are both taken to be constant such that $F_{pH}/F = \alpha$ = constant.

In the present embodiment, the salt gradient is chosen to be linear, which can be represented by the following equation:

$S(t) = S(0) + k \cdot t$ wherein $S(t)$ is the salt concentration at a time lapse t after the start of the gradient; $S(0)$ is the salt concentration at the start of the gradient; k is the slope of the gradient curve, i.e. the rate of increase of the salt concentration in the eluent with time.

For any protolytic system the equilbrium constants β can be defined based on the reactions of protolysis:

$$A^{n-} + H^+ \rightleftharpoons HA^{(n-1)-}; \beta_1$$
$$A^{n-} + 2H^+ \rightleftharpoons H_2A^{(n-2)-}; \beta_2$$
$$\vdots$$
$$A^{n-} + mH^+ \rightleftharpoons H_mA^{(n-m)-}; \beta_m$$

The $\beta_i$ corresponding to the step i in this protolytic system, is given by:

$$\beta_i = \frac{\{H_iA\}}{\{H^+\}^i\{A\}}$$

It will be noted that the above defined equilibrium constant is the reciprocal of the dissociation constant, $K_a$, such that $$\beta = 1/K_a = 10^{pKa}.$$

In the above equation giving $\beta_i$, the proton activity may be expressed by:

$$\{H^+\} = h = 10^{-pH}$$

For each solute, the activity may be expressed as the product of the activity constant and the concentration of the solute. The equilibrium constant corresponding to step i consequently may be written:

$$\beta_i = \frac{fH_iA \cdot [H_iA]}{h^i \cdot f_A \cdot [A]} = \frac{fH_iA}{fA} \cdot \frac{[H_iA]}{h^i \cdot [A]}$$

Through the above given relationship between β and $pK_a$, the former one may easily be calculated for any buffer system from the corresponding values of $PK_a$ obtained e.g. by consulting a handbook such as the one mentioned in the footnote 2 of table 2.

The conditional constant $\beta_i'$ is introduced:

$$\beta_i' = \frac{[H_iA]}{h^i \cdot [A]}$$

which can also be written:

$$\beta_i' = \beta_i \cdot \frac{fA}{fH_iA}$$

The buffer solution comprises n protolytic systems, and if the concentration of the j:th protolytic system in the buffer solution is written $C_{0,j}$, the corresponding concentration in the final solution can be written $$C_j = C_{o,j} \cdot \frac{F_{buff}}{F}$$

$C_j$ is the sum of the concentrations of all the different protolytic species of the buffer system:

$C_j = [A_j] + [HA_j] + [H_2A_j] + \ldots$ which can also be written:

$$C_j = [A_j](1 + \sum_1^{N_j} \beta'_{j,i} \cdot h^i)$$

wherein $N_j$ is the number of protolytic steps of the system j. Introducing by defintion $\beta_0 = \beta'_0 = 1$ permits to write:

$$C_j = [A_j] \cdot \sum_0^{N_j} \beta'_{j,i} \cdot h^i$$

The concentration of titratable protons in the j:th protolytic system is:

$$C_j(H^+) = [HA] + 2[H_2A] + \ldots$$

which can also be written:

$$C_j(H^+) = [A_j] \cdot \sum_0^{N_j} i\beta'_{j,i} \cdot h^i$$

The total concentration of titratable protons in the j:th protolytic system at equilibrium is:

$$C_{tot}(H^+) = \sum_1^{n_{buff}} C_j(H^+) + [H^+] - [OH^-]$$

This concentration is equal to the concentration of admixed titratable protons, i.e. from the strong acid:

$$C_{H^+,o} = \frac{C_s \cdot F_{acid}}{F}$$

wherein $C_s$=the initial concentration of the strong acid; as well as from the j:th protolytic system:

$$C_{H^+,j} = C_{o,j} \cdot \frac{F_{buff}}{F} \cdot q_j$$

wherein q is a factor in relation to the protolytic system, i.e. corresponding to the number of titratable protons of the initially added buffer compound.

The system containing n protolytic systems, the total concentration of admixed titratable protons will be:

$$C_{tot}^o(H^+) = \frac{C_s F_{acid}}{F} + \sum_1^{n_{buff}} C_{o,j} \cdot \frac{F_{buff}}{F} \cdot q_j$$

The proton balance of the system can now be written:

$$\frac{C_s \cdot F_{acid}}{F} + \frac{F_{buff}}{F} \sum_1^{n_{buff}} C_{o,j} \cdot q_j = [H^+] - [OH^-] + \frac{F_{buff}}{F} \cdot$$

-continued $$\sum_1^{n'_{buff}} C_{o,j} \cdot \frac{\sum_o^{N_j} i\beta'_{j,i} \cdot h^i}{\sum_o^{N_j} \beta'_{j,i} \cdot h^i}$$

Introducing $f_1$=activity factor of monovalent ion and:

$$\varphi = \frac{F_{buff}}{F_{pH}} \quad 1 - \varphi = \frac{F_{acid}}{F_{pH}} \quad \alpha = \frac{F_{pH}}{F}$$

permits to write the proton balance as:

$$\alpha \cdot (1 - \varphi) \cdot C_s + \alpha \cdot \varphi \cdot \sum_1^{n_{buff}} C_{o,j} \cdot q_j = \frac{h}{f_1} - \frac{10^{-14}}{f_1 \cdot h} +$$

$$\alpha \cdot \varphi \sum_1^{n_{buff}} C_{o,j} \frac{\sum i\beta'_{i,j} \cdot h^i}{\sum \beta'_{i,j} \cdot h^i}$$

wherefrom the sought parameter is derivable:

$$\varphi = \left\{ C_s - \frac{1}{\alpha \cdot f_1}\left(h - \frac{10^{-14}}{h}\right) \right\} /$$

$$\left( \sum_1^{n_{buff}} C_{o,j} \cdot \frac{\sum i\beta'_{i,j} \cdot h^i}{\sum \beta'_{i,j} \cdot h^i} + C_s - \sum_1^{n_{buff}} C_{o,j} \cdot q_j \right)$$

The parameter $\phi$ must be iteratively calculated from this last equation since $\beta'_{i,j}$ and $f_1$ are dependent on $\phi$ due to the variation of the ionic strength. The Debye-Hückel equation is used to this end:

$$\log f_z = -0,51 \cdot Z^2 \cdot \frac{\sqrt{I}}{1 + \sqrt{I}}$$

$$A^{Z_B} + iH^+ \rightleftharpoons H_iA^{Z_s}$$

$$\log \beta'_i = \log \beta_i + \log f_A - \log f_{H_iA}$$

$$\log \beta'_i = \log \beta_i + 0,51\frac{\sqrt{I}}{1+\sqrt{I}}(Z_s^2 - Z_B^2)$$

In a preferred embodiment of the invention a correction factor is also used to compensate for the deviation of the actual pH of the liquid mixture from the setpoint. The compensating correction is based on the deviation from the setpoint pH of the pH measured in the liquid mixture flow F when the combined flow $F_{grad}$ of the salt solution component (iii) and the water component (iv) is constituted of only the salt solution component $F_{salt}$ (correction factor 100%B) on the one hand, and of only the water component $F_{aq}$ (correction factor 0%B) on the other hand. In both cases the correction factor is simply equal to the difference between the measured and the setpoint values. As an example, if the setpoint pH is pH=7 while at 0% of the salt solution component (i.e. $F_{grad}=F_{aq}$) a pH=6.9 is measured in the liquid mixture flow F, then a correction factor (0%B) of 0.1 is used such that the setpoint pH is chosen to be pH=7.1. This corrected value then is used (as $h=10^{-pH}$) at any salt concentration for calculating $\phi$.

The correction factor (100%B) obtained from the difference of the measured pH and the setpoint pH at 100% of the salt solution component ($F_{grad}=F_{salt}$) is used in a slightly different manner. First, φ is calculated at 100% of the salt solution component with the pH corrected by use of the correction factor 0%B ($\phi_{0\%}$), as well as with the pH corrected by the use of the correction factor 100%B ($\phi_{100\%}$). Then the difference of these two values is calculated:

$$\Delta\phi_{100\%} = \phi_{0\%} - \phi_{100\%}.$$

This difference finally is used as a correction factor for φ at any salt concentration. This may be performed e.g. as a linear correction according to the equation:

$$\phi_{korr} = \phi - \Delta\phi_{100\%} \cdot F_{salt}/F_{grad}.$$

Other relationships than the above given linear equation may also be used to establish a corrected value of φ on the basis of its calculated, uncorrected value and the increment $\Delta\phi_{10-0\%}$. As an example, a non-linear relationship may be empirically established, such as the equation:

$$\varphi_{korr} = \varphi - \Delta\varphi_{100\%} \cdot g \cdot \frac{\sqrt{Fsalt/Fgrad}}{1 + r \cdot \sqrt{Fsalt/Fgrad}}$$

wherein g and r each represent numbers to be empirically determined, e.g. g=2 and r=1.

In a preferred embodiment the range from 0% to 100% of $F_{salt}/F_{grad}$ is subdivided in several intervals, and for the start and end points of each interval the above given non linear equation is applied to calculate a corresponding value of $\phi_{korr}$. Linear interpolation then is performed between these values.

By the method of the invention, the pH of the eluent can be set with an accuracy of +/−0.3, more preferably +/−0.1, at a varying ionic strength.

As stated above, in a preferred embodiment of the method of obtaining a liquid flow of the invention, the components (i) and (ii), i.e. the buffer solution and the acid/base solution, are fed together by use of a valve connected to a pump, the two other components, i.e. (iii) and (iv) being fed in a similar way by another valve and pump system. The metering device of the invention thus comprises two sets of a valve and pump, which in the chromatographic system of the invention preferbly are on-line with the separation device (e.g. the chromatographic column).

The other parts comprised in the chromatographic apparatus of the invention could be any of those conventionally used within the field of the art, as described in e.g. Poole C. F. and Poole S. K., "Chromatography today", 1rst ed., Elsevier Science B.V., Amsterdam, Netherlands, (1991) incorporated herein by reference.

The method of the invention can advantageously be applied to the optimization of the separations and purifications of biomolecules such as proteins, as well as to the study of the robustness of these separations/purifications.

As an example, to optimize a protein separation one may first proceed to a salt gradient elution at several different pH's at rather large intervals, e.g. pH 4, pH 5, pH 6 . . . , pH 10; this optimization is called "pH screening". One may then proceed to a finer optimization of the pH, e.g. in performing elutions at smaller pH intervals around the optimum value found from this first pH screening.

A study of the robustness of the separation towards pH variations also can be performed, by varying the pH with small increments around the pH selected for the elution.

The invention will be further illustrated by way of the present examples.

EXAMPLES

In the examples 1 and 2, the optimization of protein separations with the method of the invention will be described. The parameter that is varied being the pH, the optimization is called "pH-screening". At the finally selected optimum pH, the separation obtained is compared to the separation which is obtained with the traditional way of performing an ionic strength gradient at a selected pH, i.e. by the mixing of two buffers both having the selected pH, but differing in ionic strength. It will be seen that equivalent separation is obtained.

Furthermore, the pH of the liquid eluent mixture obtained with the method of the invention, will be measured during salt gradients of the above type.

Experimental

The proteins to be separated were transferrin (sigma T-4515), ovalbumin (Sigma A-55o3), beta-lactoglobulin (Sigma L-6879), Chymotrypsinogen A (Pharmacia 17-0442B lot 2100442011), Cytochrome C (horse heart) (Sigma C-2506) and Lysozyme (Sigma L-6876).

The instrumentation used was a chromatographic device having a UV detector with a 2 mm cell and a 1.6 ml mixer. The data software was Unicorn 2.00.09 with the above described function devised to calculate the accurate proportions of the eluent components. This system is denominated ÄKTA™ explorer.

The columns were Mono Q and Mono S HR 10/10.

The buffer solutions used for the method of the invention were:

AIEX1: 0.05M 1-methyl-piperazine+0.05M Bis-Tris+ 0.02M triethanolamine;

AIEX2: 0.05M 1-methyl-piperazine+0.05M Bis-Tris+ 0.025M Tris;

CIEX: 0.03M Na$_2$HPO$_4$+0.03M Na Formate+0.06M Na Acetate.

The buffer solutions used for the "traditional method" were:

AIEX; 20 mM piperazine pH 6.0, 0–0.5M NaCl

CIEX: 50 mM MES pH 6.6, 0–1.0M NaCl.

The acid used to vary the pH in the eluent mixtures of the invention was aqueous HCl 0.1M.

The salt used for the obtention of the salt gradient was aqueous NaCl, 1.0M for the AIEX buffers and 2.0M for the CIEX buffer. In the anion exchange mode, the salt concentration of the eluent varied between 0M and 0.5M during the salt gradient; in the cation exchange mode it varied between 0M and 1.0M.

Example 1 pH Screening, Anion Exchange Mode

Figure 2:
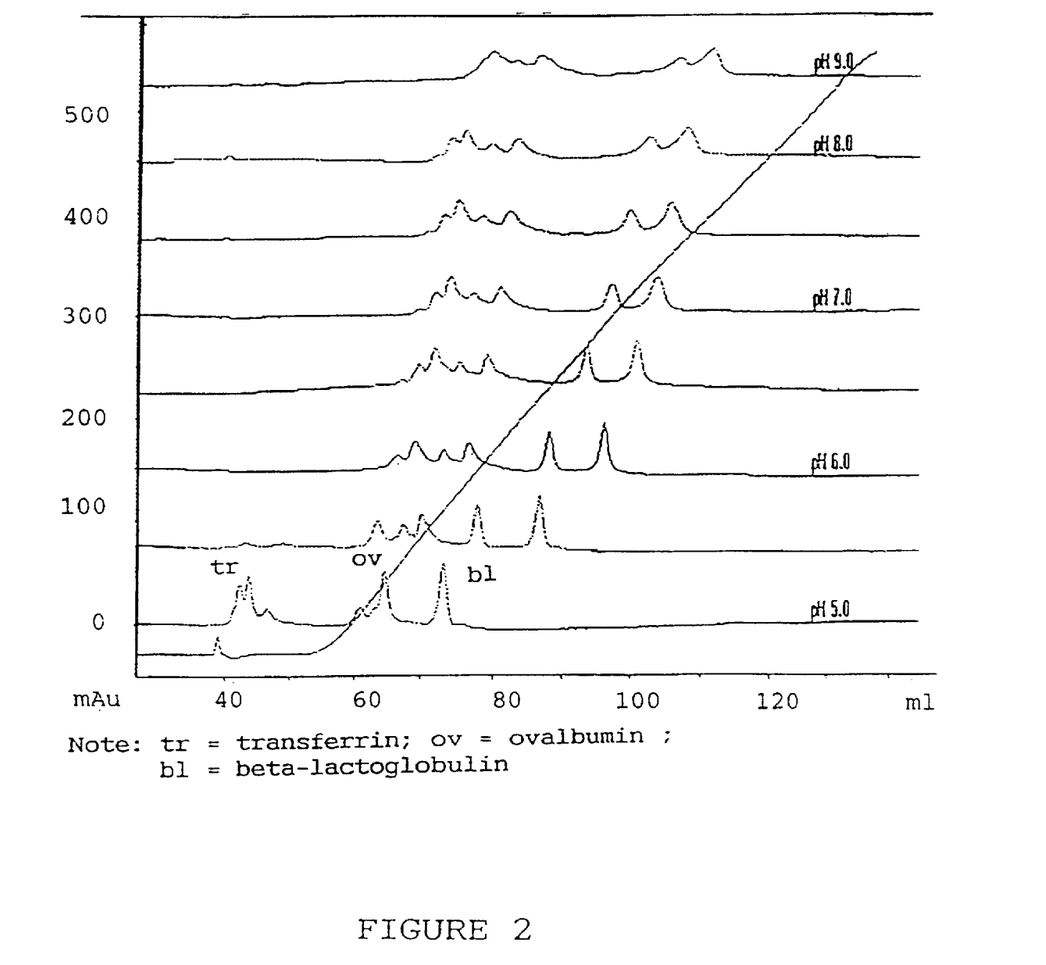
FIG. 2 represents the chromatograms obtained from a mixture of three different proteins in performing anion exchange chromatographic separations with a salt gradient at different preselected pH values using a liquid eluent mixture obtained with the method of the invention.

Samples of 500 microliters containing transferrin 2 mg/ml, ovalbumin 4 mg/ml and beta-lactoglobulin 4 mg/ml were injected on a Mono Q HR 10/10 column. The chromatographic runs then were performed at pH 5.0, 5.5, 6.0, 6.5, 7.0, 7.5, 8.0 and 9.0 by use of a liquid eluent mixture obtained with the method of the invention, comprising the buffer AIEX2. The chromatograms obtained at the respective pH's are shown in FIG. 2.

Next, the pH variation in the liquid eluent mixture of the invention during the salt gradient was investigated at the different pH's as listed above. The pH electrode was calibrated with a stationary reference buffer. In the FIG. 3 the pH vs. the salt gradient is shown.

Figure 4:
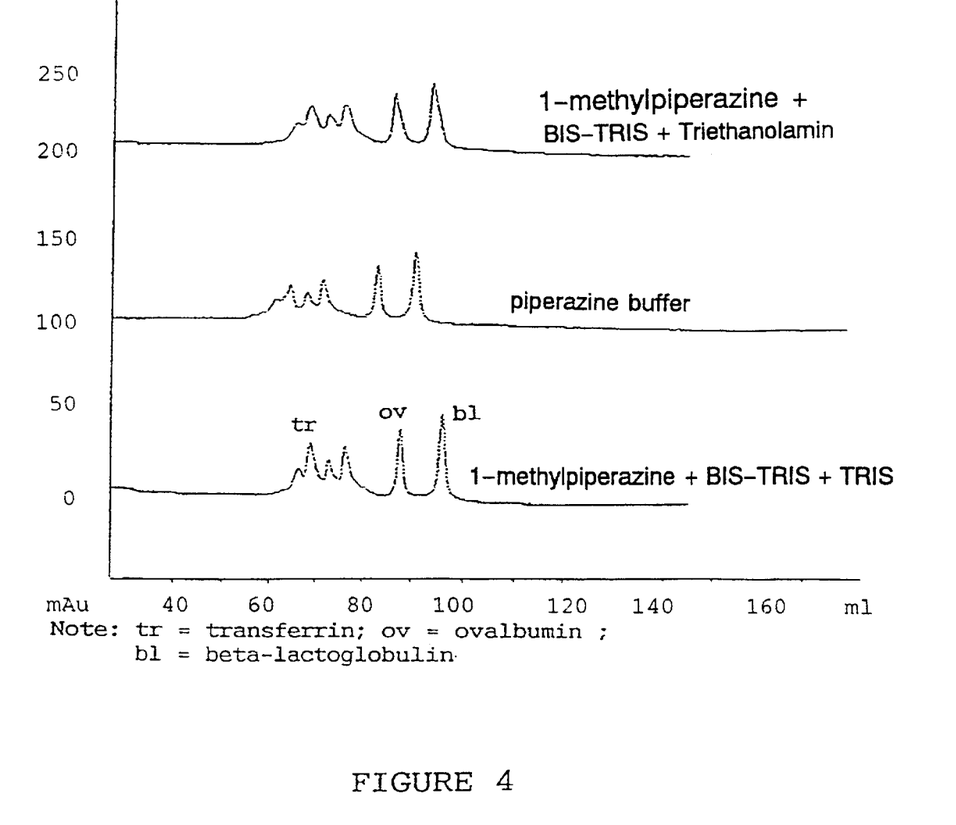
FIG. 4 represents the chromatograms obtained from a mixture of three different proteins in performing anion exchange chromatographic separations with a salt gradient at a constant pH, with a liquid eluent mixture obtained by the method of the invention and by a traditional method of the state of the art, respectively.

Furthermore, chromatographic runs were performed at pH 6—retained as optimum from the above described pH screening—with a liquid eluent mixture obtained with the method of the invention using the two different AIEX buffers of the invention and with the traditional method using the traditional AIEX buffer respectively. The chromatograms obtained are shown in FIG. 4.

Example 2 pH Screening, Cation Exchange Mode

Figure 5:
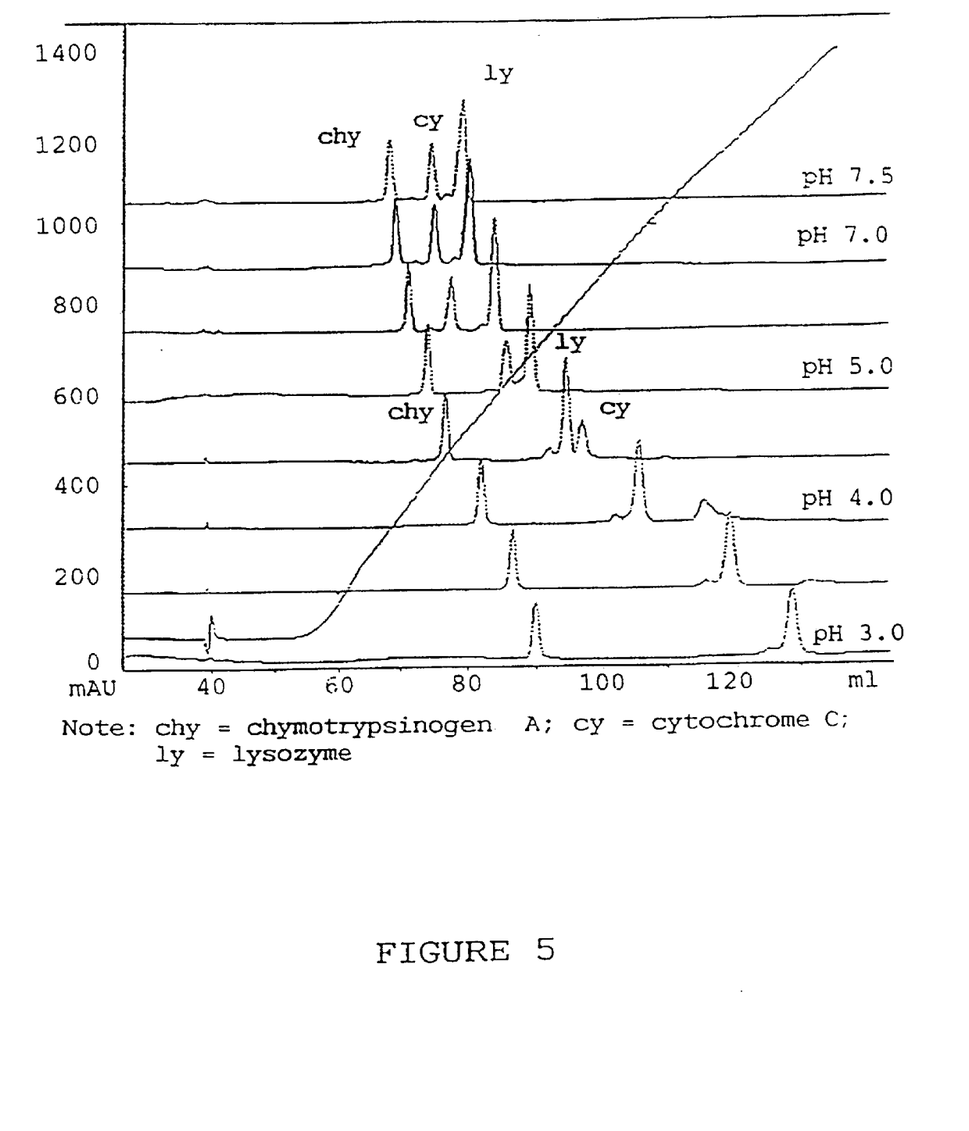
FIG. 5 represents the chromatograms obtained from a mixture of three different proteins in performing cation exchange chromatographic separations with a salt gradient at different preselected pH values using a liquid eluent mixture obtained with the method of the invention.

Samples of 500 microliters containing chymotrypsinogen A 1.25 mg/ml, cytochrome C 1.3 mg/ml and lysozyme 1.9 mg/ml were injected on a Mono S HR 10/10 column. The chromatographic runs then were performed at pH 3.0, 3.5, 4.0, 4.5, 5.0, 6.0, 7.0 and 7.5 by use of a liquid eluent mixture obtained with the method of the invention, comprising the buffer CIEX. The chromatograms obtained at the respective pH's are shown in FIG. 5.

Figure 6:
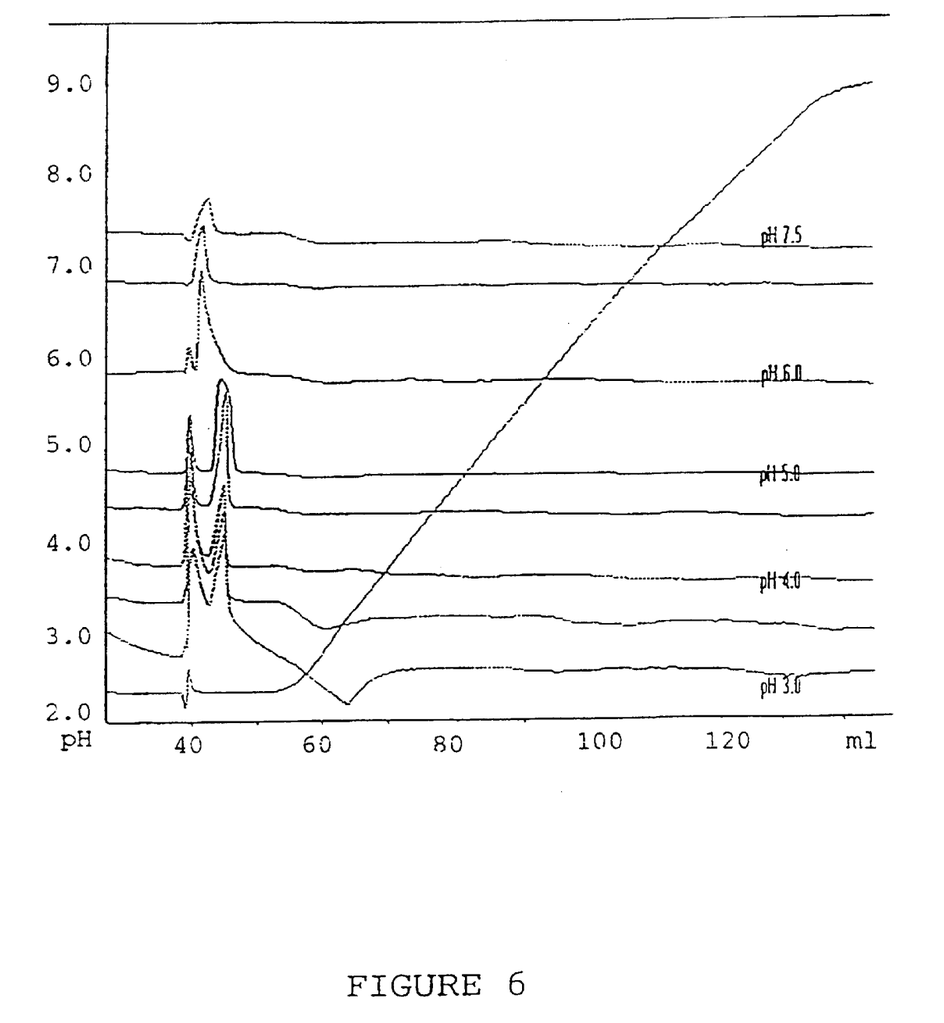
FIG. 6 represents the variation of the pH of the liquid eluent mixture, measured at the outlet side of the chromatographic column during the salt gradient of the protein separations represented in FIG. 5.

During the above cation exchange chromatographic runs the eluent pH was measured at the outlet side of the chromatographic column. The pH electrode was calibrated with a reference buffer in a flow system. The results are shown in FIG. 6.

Figure 7:
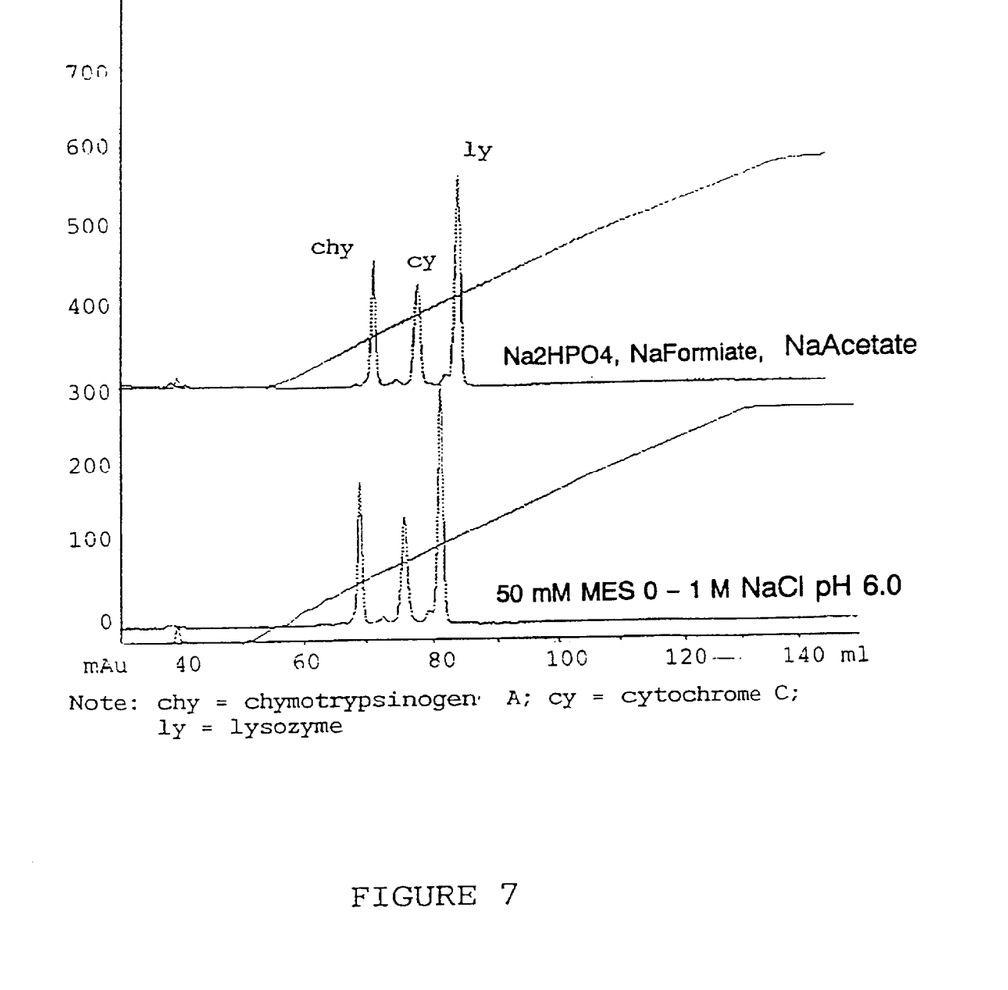
FIG. 7 represents the chromatograms obtained from a mixture of three different proteins in performing cation exchange chromatographic separations with a salt gradient at a constant pH, with a liquid eluent mixture obtained by the method of the invention and a traditional method of the state of the art, respectively.
Figure 8:
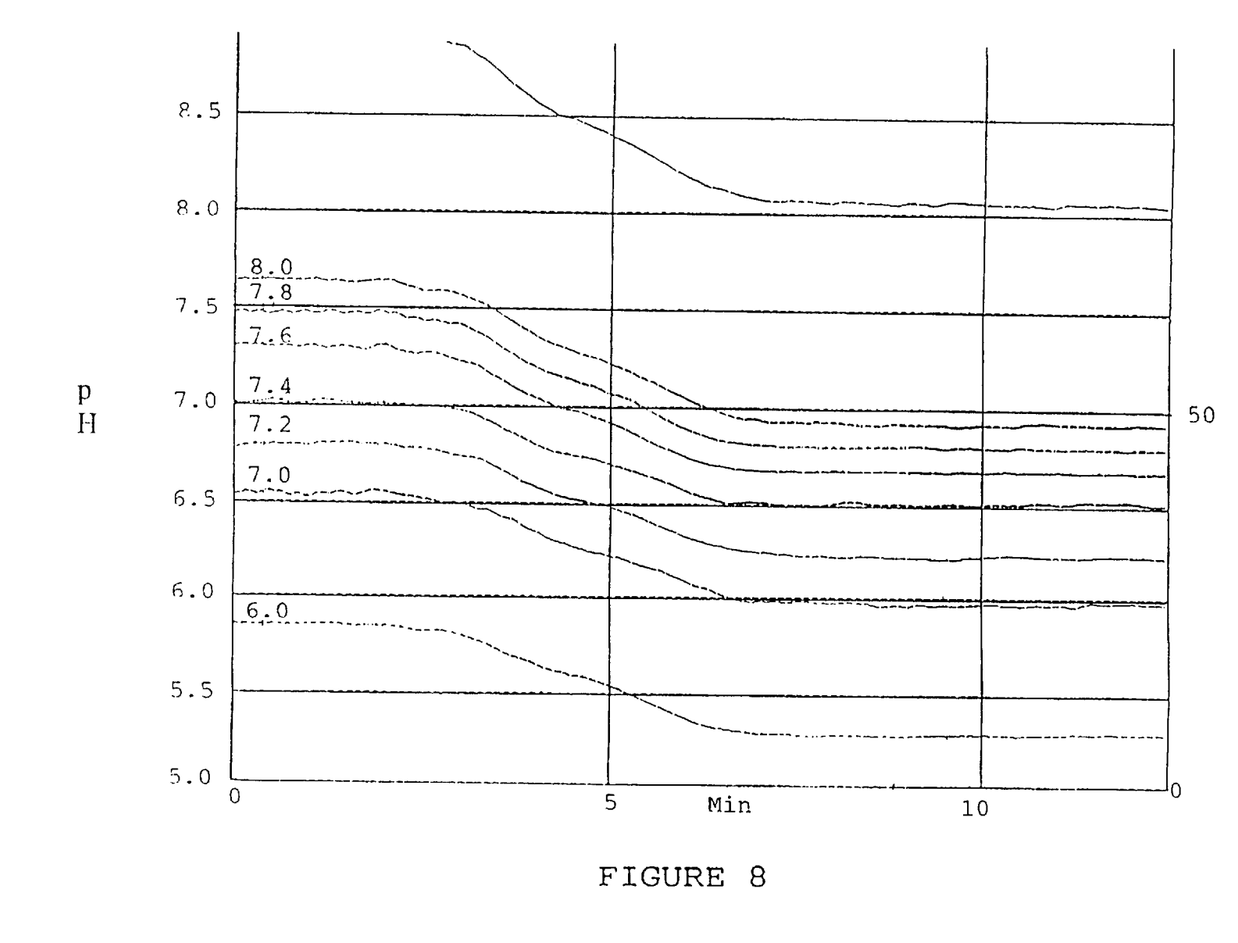
FIG. 8 represents the variation of the pH during a salt gradient in a liquid eluent mixture for anion exchange chromatography obtained with the BioCAD™ method of the prior art.

Furthermore, chromatographic runs were performed at pH 6, retained as optimum from the above described pH screening, with a liquid eluent mixture obtained with the method of the invention using the CIEX buffer of the invention and with a traditional method using the above defined "traditional" CIEX buffer respectively. The chromatograms obtained are shown in FIG. 7.

Results

Referring first to the chromatograms obtained from the pH screening of the anion exchange chromatography described in example 1, shown in the FIG. 2, it can be seen that at increasing pH the peaks corresponding to the proteins are eluting later in the gradient. The order of elution is transferrin, followed by ovalbumin and beta-lactoglobulin as the final eluted component, this elution order is retained at all pH values being screened. The best separation is obtained at pH 6.0–6.5.

From the FIG. 4 it can be seen that at this optimum pH the separation is equivalent to the one obtained with the "traditional method".

The great advantage of the method of the invention compared to the "traditional" methods thus essentially is the much easier optimization: with only one buffer solution a wide range of pH can be covered.

Figure 3:
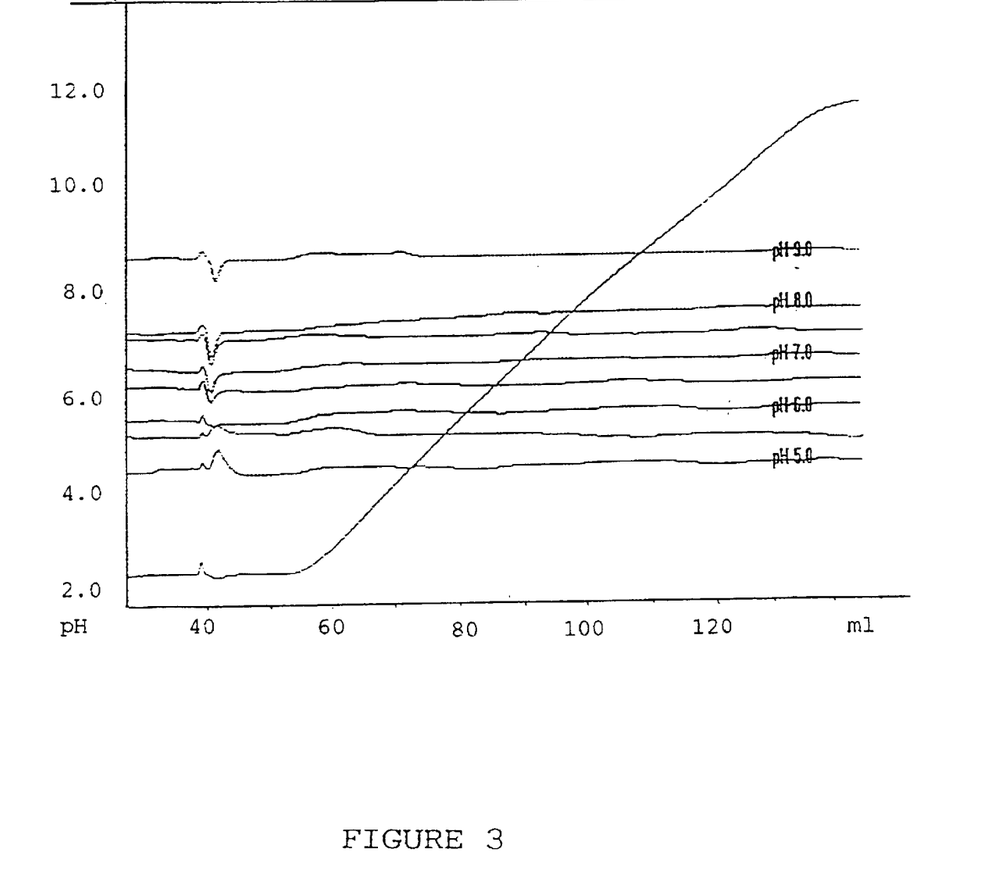
FIG. 3 represents the variation of the pH during a salt gradient in a liquid eluent mixture for anion exchange chromatography obtained with the method of the invention.

From the FIG. 3 it can be seen that the eluent pH is quite stable during the whole of the gradient. The maximum drift of the pH was obtained at pH 8, where it was 0.1 pH unit.

Further, the real difference of the set pH and the measured pH of the eluent, is in fact much smaller than it seems from FIG. 3: by the use of an external pH-meter (at pH 5, 7 and 8), it could be shown that the real difference between the set pH and the pH obtained was less than −0.1 pH unit. The apparent difference in pH is due to the calibration method of the pH-meter, using a stationary liquid instead of a flow as during the eluent pH measurement.

In the pH screening of the cation exchange chromatography, with the chromatograms shown shown in FIG. 5, there is an inversion in the order of elution of the cytochrome C and the lysozyme at increasing pH (between pH 4.5 and pH 5.0). The best separation is obtained at pH 6.

As in the preceding case it again is shown that the separation obtained with the method of the invention is equivalent to the one obtained with the "traditional" method, FIG. 7.

Also, the pH curves in FIG. 6 show that the pH is very stable during the whole salt gradient. The peaks in the beginning of the graphs and the "dip" at pH 3 are due to the pH of the sample solution medium itself passing the column and electrode.

Example 3

In this example, the drift of the eluent pH during a salt gradient, as obtained with a system in accordance with the invention and a system according to a method of the prior art, namely the BioCAD™ method, were compared.

Experimental

In the BioCAD™ method, two buffers were used to vary the pH between each run. These two buffers were obtained from an AIEX buffer comprising 0.05M Bis-Tris-propane and 0.05M Tris, which buffer had been titrated to pH 6 and pH 9, respectively. Consequently, by varying the mixing ratios of the two buffers in the buffer solution, the pH thereof could be varied between 6 and 9. This was done automatically by a function in the BioCAD™ program.

At each run, the salt gradient was obtained by use of an aqueous NaCl solution, varying from 0M to 1.0M at a rate of 0.05M/min.

The pH was measured at the outlet side of the column.

Results

Figure 9:
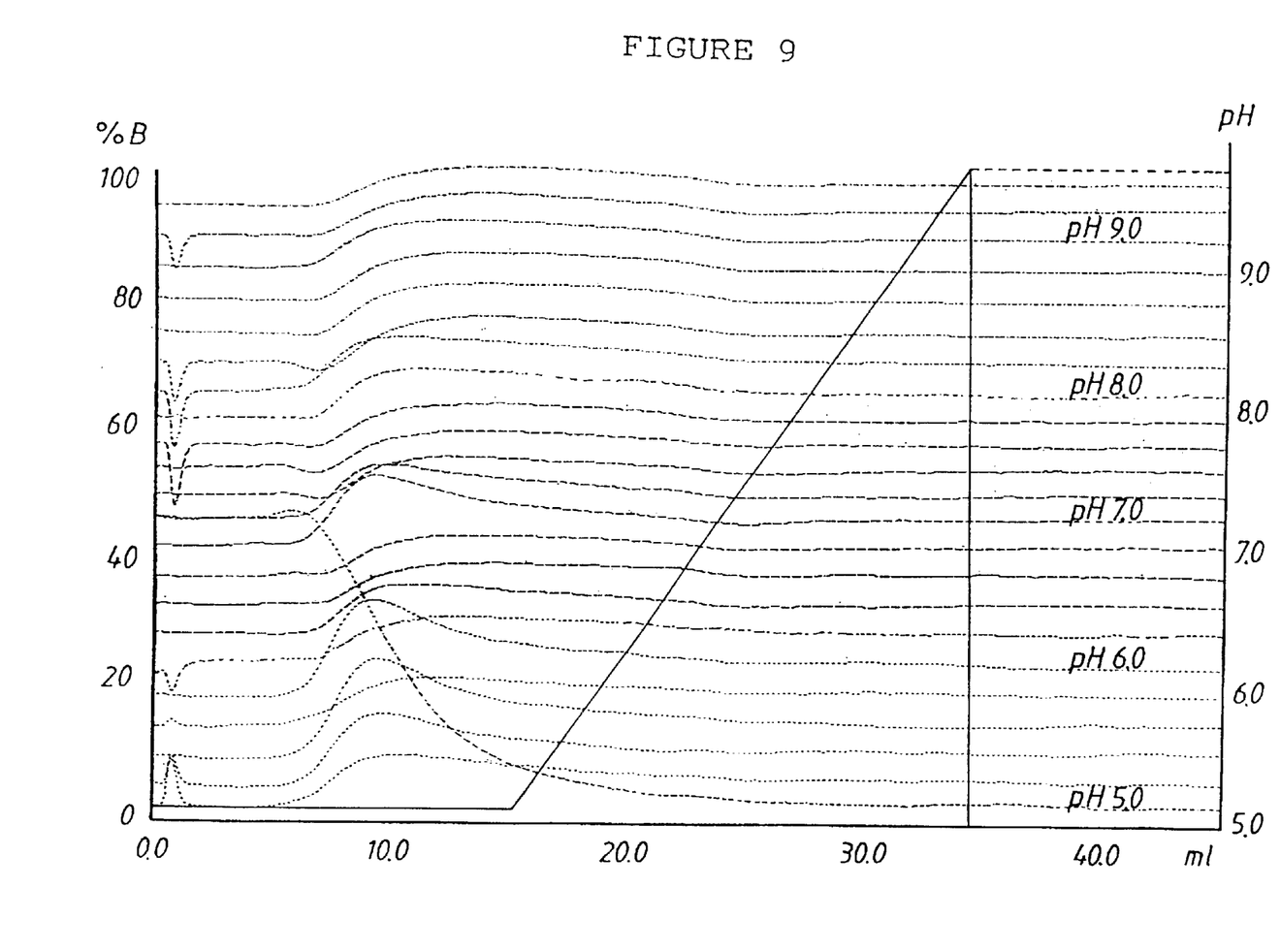
FIG. 9 represents the variation of the eluent pH during a salt gradient in a liquid eluent mixture for anion exchange chromatography obtained with the method of the invention.

In FIG. 9 the pH curves obtained with the BioCAD™ method are shown. There is a large difference between the setpoint pH and the measured pH as well as a very large pH drift during the gradient: e.g. at a setpoint pH of 7.0 the drift exceeds 0.5 pH units (from over pH 6.5 to under pH 6.0).

In contrast to this, by use of the present method, the pH obtained is seen to be very stable during the whole salt gradient, FIG. 9.

CONCLUSION

By use of the method of the invention a liquid mixture of controlled pH and ionic strength thus is obtained, and moreover the pH can be varied over a large range without having to prepare new buffers.

The application of the invention to the separation and purification of biomolecules such as proteins allows for a greater accuracy in the eluent parameters of interest, and at the same time the hitherto quite cumbersome optimization of such separations/purifications is greatly simplified.

The invention has been described as a means for keeping the pH of a liquid mixture constant at varying ionic strength. Nevertheless, the modification wherein the pH is used as another variable parameter, e.g. during a chromatographic separation with a pH gradient with or without a salt gradient, is also contemplated within the scope of the invention and the necessary changes as to the method is considered to be within the knowledge of the person skilled in the art.

What is claimed is:

1. A method of preparing an eluent comprising the following components:
   (i) one or more buffering species;
   (ii) an acid or alternatively a base;
   (iii) optionally a salt; and
   (iv) a solvent wherein the proportions of the components (i) to (iv) are concomitantly varied in such a way as to take account of the interrelationship of the pH and the ionic strength in the liquid mixture to obtain at each moment a preselected pH of the mixture.

2. The method according to claim 1, characterized in using an iterative procedure based on a modified equation of Debye-Hückel to determine said variable proportions of (i) to (iv).

3. The method according to claim 2, characterized in that the iterative procedure consists of
   (a) calculating, by the use of the Debye-Hückel equation, the proportions of the different protolytic components of a mixture as defined in claim 1 having a given salt concentration, wherein the ionic strength of said mixture is taken to be due only to the presence of said salt, to obtain a preselected pH of said mixture;
   (b) on the basis of the proportions calculated in the preceding step, calculating the resulting ionic strength of the mixture;
   (c) by use of the Debye-Hückel equation and taking account of the ionic strength calculated in (b), calculating a new set of proportions of the protolytic components of the mixture at the preselected pH of the mixture; and
   (d) repeating the steps (b) and (c) until the deviation between the last set of values found for the proportions of the protolytic components and the set found in the immediately preceding step does not exceed a predefined maximum level, this last set of proportions then being retained as yielding the mixture of the selected pH at the given salt concentration.

4. The method according to claim 3, characterized in that the components (i) to (iv) of the liquid mixture are provided as separate liquids.

5. A method according to claim 1, characterized in that the solvent is distilled and/or deionized water.

6. A method according to claim 1, characterized in that the salt is an inert salt.

7. A method of generating an eluent flow of constant pH and variable ionic strength according to any of claims 1–6, characterized in that the eluent flow is obtained by feeding said solutions of (i) to (iv) by means of a metering device preferably operating according to the method of claim 3.

8. The method of claim 7 characterized in that the metering device operates according to the method of claim 3.

9. A method according to claim 8 further comprising using said eluent flow for liquid chromotography.

10. The method of claim 9 characterized by being ion column chromatography.

11. An apparatus for liquid chromatography comprising an on-line metering device capable of feeding into a chromatographic separation device an eluent of one or more buffering species, one of an acid and a base, optionally a salt, and a solvent, wherein the proportions of said eluent are concomitantly varied in such a way as to take account of the interrelationship of the pH and ionic strength in said eluent to obtain at each moment a preselected pH of said eluent; wherein said metering device is capable of performing the steps of:
   (a) calculating, by the use of the Debye-Hückel equation, the proportions of the different protolytic components of said eluent having a given salt concentration, wherein the ionic strength of said eluent is taken to be due only to the presence of said salt, to obtain a preselected pH of said eluent;
   (b) calculating the resulting ionic strength of said eluent on the basis of the proportions calculated in step (a);
   (c) calculating a new set of proportions of the protolytic components of said eluent at the preselected pH of said eluient; and
   (d) repeating the steps (b) and (c) until the deviation between the last set of values found for the proportions of the protolytic components and the set found in the immediately preceding step does not exceed a predefined maximum level, this last set of proportions then being retained as yielding said eluent of the selected pH at the given salt concentrations.

12. The apparatus according to claim 11, characterized in that the metering device comprises two pumps, one arranged for feeding the buffer species solution and the acid (or base) solution, and the other one arranged for feeding the solvent and the optional salt solution.

* * * * *